United States Patent [19]
Faure et al.

[11] Patent Number: 5,500,399
[45] Date of Patent: Mar. 19, 1996

[54] SILICON ALLOY CONTAINING ALUMINUM, CALCIUM AND COPPER FOR THE SYNTHESIS OF ALKYL OR ARYL HALOGENOSILANES

[75] Inventors: Pierre Faure, Annecy; Thomas Margaria, Passy, both of France

[73] Assignee: Pechiney Electrometallurgie, Courbevoie, France

[21] Appl. No.: 440,929

[22] Filed: May 15, 1995

[30] Foreign Application Priority Data

May 31, 1994 [FR] France ................................. 94 06863

[51] Int. Cl.$^6$ ........................................ B01J 21/12
[52] U.S. Cl. ......................... 502/244; 428/403; 501/68; 502/232; 502/250; 556/472
[58] Field of Search ............................. 501/68; 502/232, 502/244, 250; 556/472

[56] References Cited

U.S. PATENT DOCUMENTS

| | | | |
|---|---|---|---|
| 4,500,724 | 2/1985 | Ward, III et al. | 556/472 |
| 5,061,672 | 10/1991 | Elattar | 502/244 |
| 5,094,832 | 3/1992 | Forwald et al. | 423/349 |
| 5,128,116 | 7/1992 | Forwald et al. | 423/348 |
| 5,281,739 | 1/1994 | Halm et al. | 556/472 |

*Primary Examiner*—Hoa Van Le
*Attorney, Agent, or Firm*—Dennison, Meserole, Pollack & Scheiner

[57] ABSTRACT

The invention relates to a silicon alloy intended for the production of alkyl or aryl halogenosilanes using the Rochow reaction, comprising, in percent by weight:

$0.05 < Al < 0.30$ $0.01 < Ca < 0.30$ $0.02 < O_2 < 0.20$ $0.10 < Fe < 0.50$ $0.01 < Ti < 0.15$ $x < Cu < 2 + x$ where $x = 3.2$ (% Ca) $+ 9.4$ (% Al) the remainder being silicon. The alloy according to the invention makes it possible to improve the reactivity and the selectivity of the reaction.

7 Claims, No Drawings

SILICON ALLOY CONTAINING ALUMINUM, CALCIUM AND COPPER FOR THE SYNTHESIS OF ALKYL OR ARYL HALOGENOSILANES

FIELD OF THE INVENTION

The invention relates to a particular quality of metallurgical silicon-based alloy, containing aluminum, calcium and copper in the form of various phases, metered and distributed in controlled fashion. This quality is especially adapted to the synthesis reaction of alkyl or aryl halogenosilanes.

DESCRIPTION OF RELATED ART

The synthesis of alkyl or aryl halogenosilanes (hereinafter called "silanes") by reaction at a temperature of 250° to 350° C. of a halogenated hydrocarbon on silicon in the presence of a copper-based catalyst is known from U.S. Pat. No. 2,380,995 to Rochow, issued on Aug. 7, 1945. The silicon used in the Rochow reaction is metallurgical silicon produced by carboreduction of silica in an electric arc furnace and then refined to adjust the ratio of its principal minor elements.

The idea of alloying copper to metallurgical silicon used for this synthesis has often been proposed in the past. Hence, the work by P. Trambouze: "Contribution à l'étude du mécanisme de la synthèse des méthylchlorosilanes" [Contribution to the study of the mechanism of methylchlorosilane synthesis], Bulletin de la Société Chimique de France, No. 288, 1956, pp. 1756–1765 and by G. H. Kolster et al.: "The η' and ε' phase of the system copper-silicon as solid reactants in the synthesis of dimethyl-dichlorosilane", Recueil des Travaux de Chimie, Vol. 83, 1964, pp. 737–751, have demonstrated that in this case, the active phase in the Rochow reaction was the η' phase of the SiCu alloy, based on $Cu_3Si$ which can be obtained either in the form of a catalyst mixed with the silicon powder used as the starting material, or by using an SiCu alloy containing this η' phase directly as the starting material.

Soviet Union Patent 810,707 of N. P. Lobusevich describes the use of an SiCu alloy containing from 4 to 6% copper as contact mass in the reaction.

European Patent EP 372,918 of ELKEM, relating to a silicon powder produced by atomization with the aid of a gas, mentioned the possible use of an alloy containing (by weight) from 0.25 to 0.55% iron, 0.05 to 0.45% aluminum, 0.005 to 0.20% calcium, and 1 to 6% copper.

European Patent Application EP 494,837, relating to a silicon powder with low superficial oxidation, also mentions the possibility of using SiCu alloys containing from 1 to 8% copper.

U.S. Pat. No. 5,281,739 assigned to Dow Corning describes a process of preparing silanes with the aid of an giCu alloy containing from 0.01 to 9% copper freed of its dross. It ascribes the fluctuations in yield confirmed in the Rochow reaction to the oxygen distributed in the mass of the alloy, in the form of inclusions of dross, and proposes to eliminate this oxygen by adding copper to the liquid silicon and by separating the dross, until an oxygen content that is not specified is obtained.

Hence, until now it has always been acknowledged that in view of the binary Si-Cu diagram, it was sufficient to add copper to the liquid silicon in order upon solidification to obtain the phases Si and $Cu_3Si$ in the form of primary silicon and the eutectic constituted between Si and the η' phase.

SUMMARY OF THE INVENTION

Research by the applicants has now demonstrated that obtaining elevated production in the Rochow reaction was not linked simply to reducing the ratio of oxygen and increasing the ratio of copper in the alloy, but rather had more to do with control of the various intermetallic compounds in its metallurgical structure, which compounds involve not only the copper but also the aluminum and the calcium that are present in the alloy.

Thus, the invention is directed to a silicon alloy intended for the production of alkyl or aryl halogenosilanes comprising, by weight:

0.05<Al<0.30%
0.01<Ca<0.30
$0.02<O_2<0.20$
0.10<Fe<0.50
0.01<Ti<0.15
x<Cu<2+x
where x=3.2 (% Ca)+9.4 (% Al)
the remainder being silicon.

DETAILED DESCRIPTION OF THE INVENTION

The Rochow reaction, which is the basis for the silicone industry, is generally performed with methyl chloride and leads to a mixture of different methylchlorosilanes, the only one of which sought is dimethyldichlorosilane (D). The productivity of the reaction is accordingly the product of two factors: the quantity Q of silanes produced per unit of time, which is called reactivity, and the proportion $\alpha_2$ of compound D in the silanes formed. The object is to obtain both elevated productivity $\alpha_2 Q$ and maximal selectivity, that is, a proportion $\alpha_2$ as close as possible to 1.

In preparing alloys of various compositions by melting, beginning with metallurgical silicon and electrolytic copper, and studying the structure of these alloys in the solid state by scanning electron microscopy, one observes the presence of four intermetallic copper-based compounds: $Cu_4SiAl$, $Cu_2Si_3Al$, $Cu_2Si_3Ca$ and $Cu_3Si$. Examining the specimens with increasing copper content, one finds, against every expectation, that the $Cu_3Si$ phase appears only when all the aluminum and calcium are engaged in the corresponding intermetallic compounds, and that the $Cu_3Si$ phase is not obtained unless the composition of the alloy meets the following relationship (R):

(% Cu)>3.2 (% Ca)+9.4 (% Al)

The titanium and the iron present in trace amounts do not enter into this relationship.

By subjecting the specimens to a silane production test, one confirms that the alloys whose composition meets the relationship (R) gives better results than others, both for reactivity and for selectivity. One also confirms that alloys strongly overdosed with copper relative to the relationship (R) do not produce to better results than those that meet (R) but with a slight excess of copper.

Finally, contrary to the teaching of U.S. Pat. No. 5,281,739, it appears that the oxygen content of the alloy has no significant influence on the reactivity and the selectivity of the synthesis.

These observations, linked with practical considerations that lead to providing a certain safety margin above the theoretical limit and economic considerations which mitigate against any unnecessary excess of copper, make it possible to determine an optimum copper content around 1+x, where:

$$x=3.2 \text{ (\% Ca)} + 9.4 \text{ (\% Al)}$$

and to find the valuable composition range at:

$$x < (\% \text{ Cu}) < 2+x,$$ and preferably:

$$x+0.5 < (\% \text{ Cu}) < 1.5+x.$$

In the preparation of alloys according to the invention, the copper is generally introduced into the liquid silicon in metallic form, for example with the aid of chips or other suitable scraps. Some of the copper may also originate in an arc furnace electrode, particularly in the case where a self-baking electrode of the Söderberg type is used, an electrode in which a carbon-containing paste is baked in the course of its progressive descent through a furnace inside a cylindrical casing. The choice of a copper casing instead of a steel casing which is conventionally used with Söderberg electrodes makes it possible to reduce the iron content in the alloy and to increase its copper content. In order for the carbon-containing paste to be sufficiently well baked at the end of its descent, it is useful to use contact plates, pressed against the electrodes in order to supply them with electric current, the contact plates being provided with special cooling devices that allow keeping them at high temperature, as described in French Patent Application No. 2,697, 398.

The alloy according to the invention can be prepared in the form of a powder by crushing ingots and grinding them in a low-reactivity atmosphere, in such a way as to obtain particles with only slight superficial oxidation, covered with an oxide film of less than 2 nm in thickness, as described in European Patent Application EP 494,837.

The alloy of the invention can also be obtained by granulation, for example granulation in water and in an inert atmosphere, by using a refractory dish onto which a jet of liquid alloy falls in a shower of droplets, which drop into a container filled with water, where they solidify, as described in French Patent Application No. 93-10257, filed Aug. 20, 1993, published as Application No. 2,709,082 on Feb. 24, 1995. The alloy can also be atomized in inert gas. The grinding and storage of the powder are advantageously done in the absence of air.

The microstructure of the alloy will preferably be controlled in such a way that all the intermetallic compounds, whether or not they contain copper, are in the form of well-dispersed phases, as described in French Patent Application No. 94-02487, filed Feb. 25, 1994, corresponding to U.S. Pat. application No. 08/390,022 filed Feb. 17,1995; that is, when an image of the microstructure obtained with the scanning electron microscope is processed by binarization between an intermetallic phase and a silicon matrix, followed by enlargement of the zones corresponding to the intermetallic phase with an extension of 10 μm around these zones, the ratio $S/S_0$ of the surface fractions of the intermetallic phase between the expanded image and the image before enlargement is between 20 and 40.

EXAMPLES

Example 1

An alloy with 13% Si corresponding to the composition of the η' phase of the Si-Cu equilibrium diagram is made by melting electrolytic copper and metallurgical silicon in an induction furnace. The product obtained is cooled, solidified, ground and then screened between 50 and 160 μm.

A metallurgical silicon screened between 70 and 160 μm is also prepared, to which the following are added in metered fashion (by weight):

Al=0.185% Ca=0,105% Fe=0.32%

40 g of this silicon is mixed with 2.5 g of the SiCu alloy, and a silane production test is performed on the mixture obtained. This test consists of placing the powder mixture, with 0.05 g of ZnO added, in a glass reactor 30 mm in diameter, provided with an agitator. Methyl chloride is passed into the agitated alloy bed through a fritted glass disk. The flow of methyl chloride is kept constant at $3.6 \times 10^{-3}$ m³/h. After heating of the reaction mixture and startup of the reaction, the system temperature is kept at 300° C.

After four tests of this type, the mean results are as follows:

$Q=7.8$ g/h $\alpha_2=83\%$

Example 2

Beginning with liquid metallurgical silicon sampled in production from an industrial foundry ladle, an addition of electrolytic copper is made with a view to a content in the vicinity of 0.7 x. Once the alloy is poured and solidified, the following contents are measured (by weight):

Cu=1.61% Al=0.181% Ti=0.031%

Ca=0.120% Fe=0.33% O₂=0.035%

In this alloy, the silane production test described in the preceding example is performed. The mean results for four tests are as follows:

$Q=5.6$ g/h $\alpha_2=73\%$

In this case, where x=2,085 and (% Cu)=0.77 x, it is confirmed that the reactivity and the selectivity are smaller than in the preceding case with the η' intermetallic phase.

Example 3

Example 2 is repeated, but with alloys having higher copper contents. To this end, three successive additions of copper are made, followed each time by partial pouring of the contents of the ladle.

Three analysis specimens are thus obtained, as follows (in weight %):

| No. | Cu | Al | Ca | Fe | O₂ | x |
| --- | --- | --- | --- | --- | --- | --- |
| 1 | 3.31 | 0.193 | 0.115 | 0.36 | 0.042 | 2.182 |
| 2 | 4.93 | 0.186 | 0.112 | 0.37 | 0.041 | 2.106 |
| 3 | 11.51 | 0.177 | 0.117 | 0.39 | 0.044 | 2.034 |

The same silane production test as in the preceding examples, repeated four times for the above three alloys, gave the following mean results:

| No. | Q g/h$\alpha_2$ (%) |
| --- | --- |
| 1 | 8.088 |
| 2 | 8.287 |
| 3 | 8.385 |

Specimen No. 1, in accordance with the invention, has a reactivity and a selectivity that are clearly improved compared with that of Example 2. Specimens No. 2 and 3, although provided with marked excesses of copper, are not improved in performance.

Example 4

The alloys of Example 3 are individually remelted in an induction furnace under a vacuum, then poured in a vacuum so as to obtain alloys that have an oxygen content that will be as low as possible.

The products obtained are reanalyzed and yield the following compositions (in weight %):

| No. | Cu | Al | Ca | Fe | $O_2$ |
|---|---|---|---|---|---|
| 1' | 0.92 | 0.191 | 0.107 | 0.42 | 0.017 |
| 2' | 4.51 | 0.182 | 0.098 | 0.42 | 0.014 |
| 3' | 9.72 | 0.170 | 0.102 | 0.43 | 0.015 |

The silane production test, performed four times with each of these re-treated alloys, gave the following mean results:

| No. | Q (g/hα)$_2$ (%) |
|---|---|
| 1' | 8.089 |
| 2' | 8.387 |
| 3' | 8.286 |

Given the level of precision of the results, one cannot conclude that there was any significant improvement in the performance associated with the lowering of the oxygen content.

Example 5

Beginning with liquid metallurgical silicon samples in production from a foundry ladle, an addition of copper is made, seeking a content of 1+x, hence 3.2%, knowing that Al =0.20% and Ca=0.10% are sought.

The silane production test is performed on the product obtained, and the operation is begun again for two consecutive weeks from Monday to Friday. The following results were obtained:

| Al % | Ca % | Cu % | Fe % | Ti % | $O_2$ % | Q % | $\alpha_2$ % |
|---|---|---|---|---|---|---|---|
| 0.214 | 0.107 | 3.52 | 0.34 | 0.030 | 0.045 | 8.02 | 89.3 |
| 0.187 | 0.098 | 3.41 | 0.37 | 0.029 | 0.047 | 8.17 | 87.6 |
| 0.193 | 0.092 | 3.27 | 0.32 | 0.032 | 0.041 | 7.81 | 87.9 |
| 0.207 | 0.109 | 3.11 | 0.34 | 0.034 | 0.037 | 7.87 | 88.9 |
| 0.198 | 0.104 | 3.27 | 0.35 | 0.031 | 0.053 | 8.21 | 88.3 |
| 0.213 | 0.112 | 3.45 | 0.36 | 0.029 | 0.030 | 8.07 | 87.2 |
| 0.194 | 0.088 | 3.28 | 0.39 | 0.030 | 0.063 | 8.12 | 88.4 |
| 0.189 | 0.094 | 3.07 | 0.43 | 0.029 | 0.047 | 7.98 | 86.8 |
| 0.208 | 0.103 | 3.15 | 0.32 | 0.031 | 0.052 | 7.95 | 87.7 |
| 0.208 | 0.105 | 3.23 | 0.34 | 0.031 | 0.048 | 8.33 | 88.6 |
| | | | | mean: | 0.046 | 8.05 | 88.1 |
| | | | | **: | | 0.160 | 0.775 |

** = standard deviation

The product poured, which was not used for the test and remained in pieces, is remelted in the induction furnace under a vacuum, repoured in a vacuum, then ground and again subjected to the silane production test. The following results were obtained:

| Al % | Ca % | Cu % | Fe % | Ti % | $O_2$ % | Q % | $\alpha_2$ % |
|---|---|---|---|---|---|---|---|
| 0.194 | 0.098 | 3.47 | 0.37 | 0.030 | 0.014 | 8.12 | 89.0 |
| 0.168 | 0.087 | 3.29 | 0.41 | 0.029 | 0.016 | 8.26 | 87.5 |
| 0.198 | 0.087 | 3.10 | 0.36 | 0.033 | 0.015 | 7.86 | 89.1 |
| 0.201 | 0.107 | 3.01 | 0.38 | 0.034 | 0.017 | 7.83 | 89.3 |
| 0.192 | 0.089 | 3.15 | 0.37 | 0.031 | 0.021 | 8.17 | 88.6 |
| 0.197 | 0.104 | 3.27 | 0.39 | 0.030 | 0.013 | 8.00 | 87.8 |
| 0.188 | 0.085 | 3.17 | 0.44 | 0.031 | 0.024 | 8.08 | 89.7 |
| 0.175 | 0.088 | 2.98 | 0.45 | 0.030 | 0.019 | 7.92 | 88.6 |
| 0.199 | 0.093 | 3.03 | 0.34 | 0.031 | 0.017 | 8.22 | 88.8 |
| 0.191 | 0.096 | 3.18 | 0.36 | 0.032 | 0.016 | 8.27 | 90.0 |
| | | | | mean: | 0.017 | 8.07 | 88.9 |
| | | | | **: | | 0.163 | 0.773 |

** = standard deviation

It is confirmed that in both cases, the means and the standard deviations for the reactivity and selectivity are not significantly different, and that the pronounced decrease in oxygen led neither to an increase in these values nor to a reduction in their fluctuations.

What is claimed is:

1. A silicon alloy for the production of alkyl or aryl halogenosilanes comprising, in percent by weight:

0.05<Al<0.30;

0.01<Ca<0.30;

0.02<$O_2$<0.20;

0.10<Fe<0.50;

0.01<Ti<0.15;

x<Cu<2+x where x=3.2 ( % Ca )+9.4 (% Al); and the remainder, silicon.

2. The alloy of claim 1, wherein 0.5+x<Cu<1.5+x.

3. The alloy of claim 1, in the form of a powder of granules with low superficial oxidation, coated with an oxide film of less than 2 nm in thickness.

4. The alloy of claim 1, prepared by granulation.

5. The alloy of claim 1, prepared by atomization.

6. The alloy of claim 1, conditioned by grinding and storage in the absence of air.

7. The alloy of claim 1, having a microstructure controlled in such a way that when an image of the microstructure obtained with the scanning electron microscope is processed by binarization between an intermetallic phase and a silicon matrix, followed by enlargement of the zones corresponding to the intermetallic phase with an extension around these zones of 10 μm, a ratio S/S$_0$ of the surface fractions of the intermetallic phase between the expanded image and the image before enlargement is between 20 and 40.

* * * * *